US009519067B1

United States Patent
Kitaguchi et al.

(10) Patent No.: US 9,519,067 B1
(45) Date of Patent: Dec. 13, 2016

(54) RADIOACTIVE GAS MEASUREMENT APPARATUS AND FAILED FUEL INSPECTION APPARATUS

(75) Inventors: Hiroshi Kitaguchi, Naka (JP);
Takahiro Tadokoro, Hitachi (JP);
Katsunori Ueno, Hitachi (JP); Hitoshi Kuwabara, Hitachi (JP)

(73) Assignee: HITACHI, LTD., Tokyo (JP)

(*) Notice: Subject to any disclaimer, the term of this patent is extended or adjusted under 35 U.S.C. 154(b) by 2097 days.

(21) Appl. No.: 12/886,616

(22) Filed: Sep. 21, 2010

(51) Int. Cl.
*G01T 1/18* (2006.01)
*G01T 1/185* (2006.01)
*G01T 1/29* (2006.01)
*H01J 47/06* (2006.01)
*H01J 47/02* (2006.01)

(52) U.S. Cl.
CPC .............. *G01T 1/185* (2013.01); *G01T 1/2935* (2013.01); *G01T 1/18* (2013.01); *H01J 47/02* (2013.01); *H01J 47/06* (2013.01)

(58) Field of Classification Search
CPC ........... H01J 47/02; H01J 47/06; G01T 1/185; G01T 1/18; G01T 1/2935
See application file for complete search history.

(56) References Cited

U.S. PATENT DOCUMENTS 7,151,262 B1    12/2006   Kitaguchi et al.
7,151,626 B2*   12/2006   Carlson .................... B41M 5/52
                                                        359/244

FOREIGN PATENT DOCUMENTS

| JP | 7-218638     | 8/1995 |
| JP | 2001-141829  | 5/2001 |
| JP | 2001-235546  | 8/2001 |
| JP | 2003-004888  | 1/2003 |
| JP | 2005-9890    | 1/2005 |

* cited by examiner

*Primary Examiner* — David Porta
*Assistant Examiner* — Mamadou Faye
(74) *Attorney, Agent, or Firm* — Baker Botts L.L.P.

(57) ABSTRACT

A radioactive gas measurement apparatus comprises: a radiation measurement cell comprising an inlet pipe and a discharge pipe, the radiation measurement cell introducing and discharging a radioactive gas containing a nuclide to be measured and a positron emitter nuclide through the inlet pipe and the discharge pipe; a radiation detector for measuring a radiation generated from the radioactive gas; and a radiation collimator allowing the radiation measurement cell to communicate with the radiation detector and setting a predetermined radiation measurement geometry condition between the radiation measurement cell and the radiation detector. Then, as the predetermined radiation measurement geometry condition, an inner wall area of the radiation measurement cell which the radiation detector views through the radiation collimator is set equal to or less than a half of a total inner wall area of the radiation measurement cell.

10 Claims, 8 Drawing Sheets

FIG.7A    FIG.7B    FIG.7C
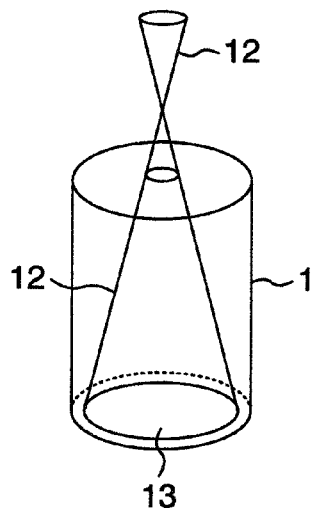
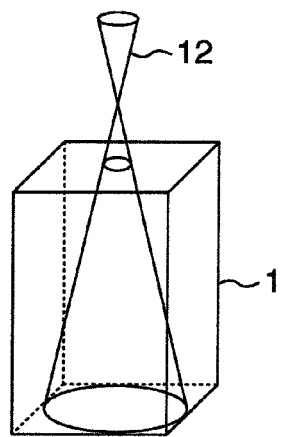
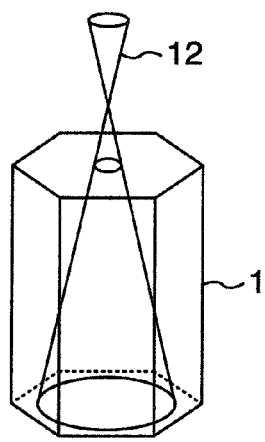
FIG.8
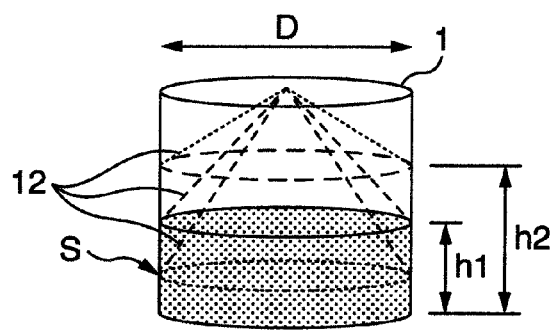
FIG.9
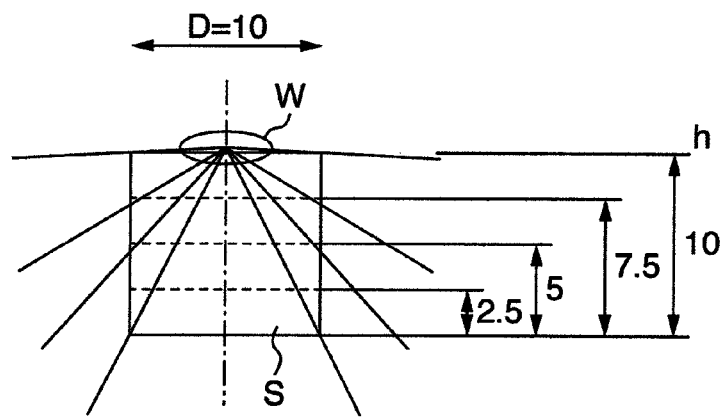

SQUARE CYLINDRICAL CELL h/D=1

VERTICAL RECTANGULAR CYLINDRICAL CELL h/D=3

CONICAL COLUMNAR CELL h/D=2 de US 9,519,067 B1

RADIOACTIVE GAS MEASUREMENT APPARATUS AND FAILED FUEL INSPECTION APPARATUS

BACKGROUND OF THE INVENTION

Field of the Invention

The present invention relates to radioactive gas measurement apparatuses. In particular, the present invention relates to a positron annihilation gamma ray suppression type radioactive gas measurement apparatus (hereinafter, also referred to as a "radioactive gas measurement apparatus") and failed-fuel detection system which measure the radiation generated from a nuclide to be measured by significantly suppressing the influence of an annihilation gamma ray from a radioactive gas containing the nuclide to be measured and a positron emitter nuclide.

Description of the Related Art

Conventionally, in a nuclear power plant, the amount of a fission product contained in a primary coolant (nuclear reactor water) or a main steam is always monitored for the purpose of confirming the soundness of a nuclear reactor fuel. In particular, the nuclear reactor water or main steam often contains a lot of N-13 (nitrogen-13). For this reason, in the measurement of an index nuclide (I-131 (iodine-131) or Xe-133 (xenon 133)) for monitoring the soundness of this failed fuel, a measurement technique for suppressing the influence of a background radiation caused by an annihilation gamma ray which N-13 radiates is indispensable.

Conventional radioactive gas measurement apparatuses and failed-fuel detection systems are described. JP-A-7-218638 discloses a failed-fuel detection system which detects the I-131 concentration in nuclear reactor water using a prior art measurement method for suppressing positron annihilation gamma rays. In the apparatus described in JP-A-7-218638, the influence of an annihilation gamma ray emitter nuclide contained in nuclear reactor water is reduced by performing an anticoincidence processing on the positron annihilation gamma ray with the use of two radiation detectors, and then 1-131 which is the index for failed fuel detection is measured.

In addition, JP-A-2001-235546 discloses a radioactive gas measurement apparatus and a failed-fuel detection system which detect the radiation concentration in a radioactive gas using a measurement method for suppressing positron annihilation gamma rays. In the apparatus described in JP-A-2001-235546, with respect to a radioactive gas, the influence of an annihilation gamma ray emitter nuclide contained in a radioactive gas is reduced by performing an anticoincidence processing on the positron annihilation gamma ray with the use of two radiation detectors, and then Xe-133 which is the index for failed fuel detection is measured.

FIG. 17 shows one example of the configuration of a conventional radioactive gas measurement apparatus including an anticoincidence circuit. In the conventional radioactive gas measurement apparatus shown in FIG. 17, a radioactive gas measurement cell 42 is provided in inlet/outlet pipes 40a, 40b for radioactive gas, which primarily contains a bleed gas in a reactor condenser system and is referred to as an off-gas, and an anticoincidence processing is performed using two detectors, i.e., a main detector 43 and a sub-detector 44, provided within a shield 41, to reduce the influence of an annihilation gamma ray emitter nuclide (N-13) contained in the gas, then Xe-133 which is the index for failed fuel detection is effectively measured.

These measurement apparatuses are intended to detect whether or not there is a failed fuel by reducing the influence of annihilation gamma rays by about 50% to 20% and examining the index nuclide, in the measurement of the index nuclide (I-131, Xe-133) for failed fuel detection during the normal operation of a nuclear reactor.

JP-A-2005-9890 discloses a conventional radioactive gas measurement apparatus including a mechanism to automatically vary the position of a collimator. The gas radioactive concentration measurement apparatus described in JP-A-2005-9890 comprises a collimator capable of automatically varying its position between a radioactive gas measuring vessel (measurement cell) and a radiation detector, thus enabling the radiation measurement corresponding to a range from a low level to a high level of the radioactive gas concentration to be measured in the measurement cell.

Furthermore, JP-A-2001-141829 discloses a conventional distribution measuring method for measuring a radioactivity distribution in a radioactive fluid in a pipe and a radioactivity distribution in an inner wall of the pipe using a radioactivity measurement apparatus which includes a measurement system, wherein a collimator and a radiation detector integrally move, in the pipe through which the radioactive fluid flows. In the method described in JP-A-2001-141829, the amount of radioactivity stuck to the pipe inner wall area and the amount of radioactivity of the fluid to be measured are determined by calculations from the measured values at two or more places where a measurement range of the pipe inner wall area and a measurement range of the volume of the fluid to be measured in the pipe differ, respectively, along the pipe through which the fluid to be measured flows.

SUMMARY OF THE INVENTION

Both the conventional radiation measurement apparatuses described in JP-A-7-218638 and JP-A-2001-235546 include two radiation detection systems and two anticoincidence circuits therefor in order to suppress positron annihilation gamma rays. However, because the conventional radiation measurement apparatuses described in JP-A-7-218638 and JPA-2001-235546 include two radiation detection systems and two anticoincidence circuits therefor, there is a problem that the measurement system becomes large and complicated and thus the radiation measurement apparatuses become large and expensive if its shield system is included.

Moreover, neither the conventional radiation measurement apparatus described in JP-A-2005-9890 nor the conventional radiation measurement apparatus described JP-A-2001-141829 includes a device for suppressing the influence of a positron emitter nuclide constituting an obstacle to the measurement, the positron emitter nuclide being mixed in the fluid to be measured. For this reason, the conventional radiation measurement apparatuses described in JP-A-2005-9890 and JP-A-2001-141829 have a problem that it is difficult to effectively eliminate annihilation gamma rays (511 keV) emitted from the positron emitter nuclide mixed in the fluid to be measured.

It is an object of the present invention to provide a small and low-cost positron annihilation gamma ray suppression type radioactive gas measurement apparatus and failed-fuel detection system with a simple configuration.

In order to achieve the above-described object, a radioactive gas measurement apparatus of the present invention comprises: a radiation measurement cell comprising an inlet pipe and a discharge pipe, the radiation measurement cell introducing and discharging a radioactive gas containing a nuclide to be measured and a positron emitter nuclide through the inlet pipe and the discharge pipe; a radiation detector for measuring a radiation generated from the radioactive gas; and a radiation collimator allowing the radiation measurement cell to communicate with the radiation detector and setting a predetermined radiation measurement geometry condition between the radiation measurement cell and the radiation detector, wherein as the predetermined radiation measurement geometry condition, an inner wall area of the radiation measurement cell which the radiation detector views through the radiation collimator is set equal to or less than a half of a total inner wall area of the radiation measurement cell.

Moreover, a failed-fuel detection system of the present invention comprises: a sampler for sampling a radioactive gas containing a nuclide to be measured and a positron emitter nuclide passing through a nuclear reactor fuel housed in a nuclear reactor; and a radioactive gas measurement apparatus for measuring a radiation generated from the radioactive gas sampled by the sampler, wherein the radioactive gas measurement apparatus comprises: a radiation measurement cell comprising an inlet pipe connected to the sampler and a discharge pipe, the radiation measurement cell introducing and discharging a radioactive gas containing a nuclide to be measured and a positron emitter nuclide through the inlet pipe and the discharge pipe; a radiation detector for measuring a radiation generated from the radioactive gas; and a radiation collimator allowing the radiation measurement cell to communicate with the radiation detector and setting a predetermined radiation measurement geometry condition between the radiation measurement cell and the radiation detector, wherein as the predetermined radiation measurement geometry condition, an inner wall area of the radiation measurement cell which the radiation detector views through the radiation collimator is set equal to or less than a half of a total inner wall area of the radiation measurement cell.

According to the present invention, it is possible to provide a small and low-cost positron annihilation gamma ray suppression type radioactive gas measurement apparatus and failed-fuel detection system with a simple configuration, without providing a complicated radiation measurement system for performing an anticoincidence processing or the like.

Other objects, features and advantages of the invention will become apparent from the following description of the embodiments of the invention taken in conjunction with the accompanying drawings.

BRIEF DESCRIPTION OF THE DRAWINGS

FIG. 7A shows an example of a cylindrical measurement cell of the first embodiment of the present invention.

FIG. 7B shows an example of a rectangular measurement cell of the first embodiment of the present invention.

FIG. 7C shows an example of a hexagonal measurement cell of the first embodiment of the present invention.

FIG. 8 is a view showing a relationship between the whole inner wall area of a measurement cell and the inner wall area viewed by a radiation detector.

FIG. 9 is a view showing an example of parameters for calculating the inner wall area of a measurement cell.

DETAILED DESCRIPTION OF THE INVENTION

Figure 1:
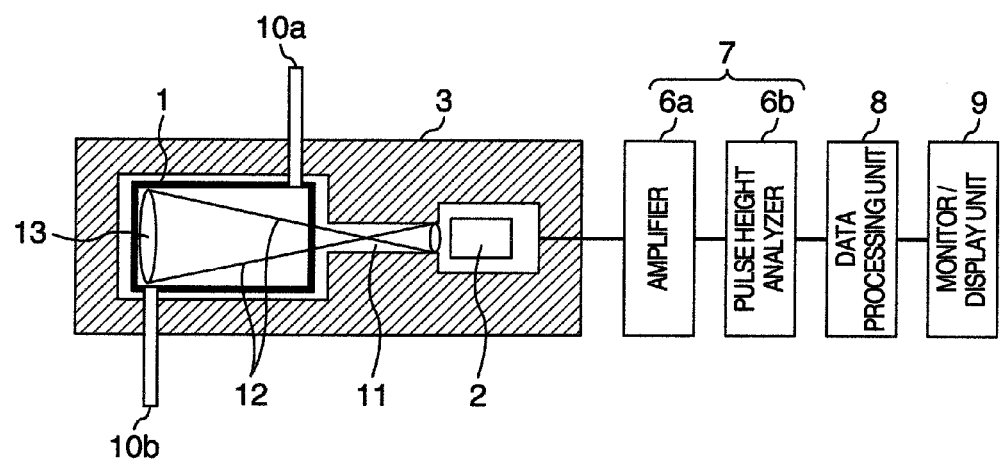
FIG. 1 is a view showing a positron annihilation gamma ray suppression type radioactive gas measurement apparatus of a first embodiment of the present invention.

Embodiments of the present invention will be described hereinafter with reference to the accompanying drawings. Note that the same constituent element is given the same reference numeral to omit the duplicated description.

FIG. 1 is a view showing a positron annihilation gamma ray suppression type radioactive gas measurement apparatus of a first embodiment of the present invention. The positron annihilation gamma ray suppression type radioactive gas measurement apparatus of this embodiment comprises: a measurement cell 1 for introducing a measurement gas; a radiation detector 2 for measuring a radiation emitted from the measurement cell 1; a shield 3 having the measurement cell 1 and the radiation detector 2 provided therein and preventing incidence of a background radiation coming from an outside of the measurement cell 1; a measured-radioactive gas inlet pipe 10a for introducing a measured gas into the measurement cell 1 from an outside of the shield 3; a measured-radioactive gas discharge pipe 10b for discharging the measured gas from the measurement cell 1; and a collimator 11 for introducing a radiation coming from the measurement cell 1 into the radiation detector 2.

Moreover, the positron annihilation gamma ray suppression type radioactive gas measurement apparatus of the first embodiment of the present invention comprises: a measurement apparatus 7 which processes detected data from the radiation detector 2 using an amplifier 6a and a pulse height analyzer 6b to measure radiation; a data processing unit 8 which analyzes and determines whether or not there is a failed-fuel detection or the like from this measured value; and a monitor/display unit 9 for displaying this result.

In the radioactive gas measurement apparatus of the first embodiment of the present invention, the shield 3 is usually formed with lead (Pb) or tungsten (W). The shield 3 is formed with iron in order to reduce the cost, depending on the use condition. Moreover, the collimator 11 defines a field of view (measurable range) within which an object to be measured in the measurement cell 1 is viewed from the radiation detector 2. The present invention defines a measurement geometry condition among the measurement cells 1, the collimator 11, and the radiation detector 2.

Figure 2:
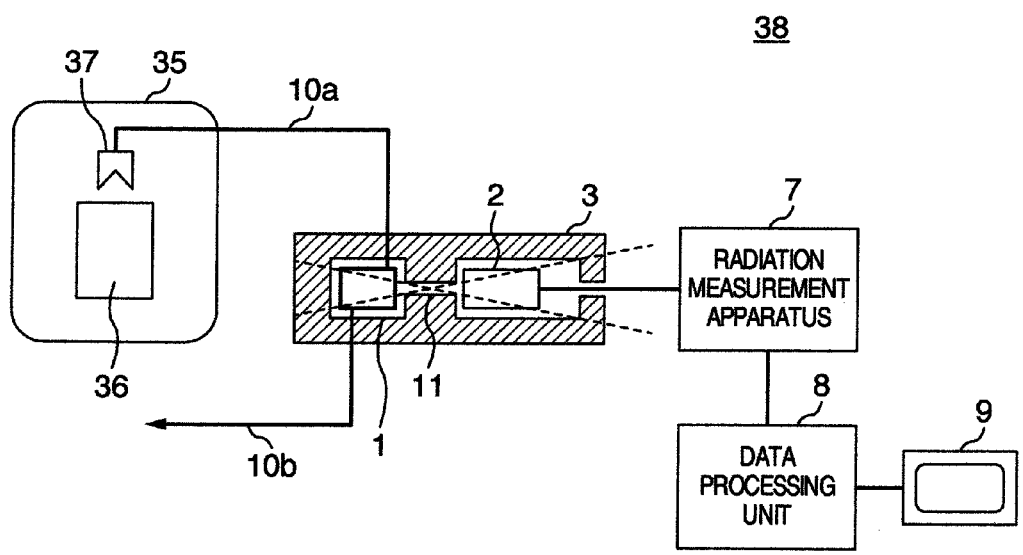
FIG. 2 is a view showing a failed-fuel detection system including the positron annihilation gamma ray suppression type radioactive gas measurement apparatus of the first embodiment of the present invention.

FIG. 2 is a view showing a failed-fuel detection system including the positron annihilation gamma ray suppression type radioactive gas measurement apparatus of the first embodiment of the present invention. The failed-fuel detection system of the present invention is installed in a nuclear reactor 35. Now, the operation of the positron annihilation gamma ray suppression type radioactive gas measurement apparatus of the present invention is described below with a case where the radioactive gas measurement apparatus is applied to the failed-fuel detection system of the present invention, as an example.

A nuclear reactor fuel 36 is housed in the nuclear reactor 35, and a measured gas passing through the nuclear reactor fuel 36 is sampled from a sampler 37. The measured gas sampled from the sampler 37 passes through a measured-radioactive gas inlet pipe 10a, flows through the measurement cell 1, and is discharged from a measured-radioactive gas discharge pipe 10b. The radiation emitted from the measured gas is measured with the radiation detector 2 and the measurement apparatus 7, through the collimator 11 provided in the shield 3. The measurement result is sent to the data processing unit 8, where whether or not there is a failed fuel or the like is analyzed and determined, and this result is displayed in the monitor/display unit 9.

Now, the principle of the present invention is described. First, the emission process of an annihilation gamma ray of a positron emitter nuclide is described with N-13 as an example. A positron emitted by N-13 has an energy of 1.19 MeV. When this positron combines with a normal negative electron existing therearound and disappears, an annihilation gamma ray is emitted. This gamma ray simultaneously generates two gamma rays (511 keV) in opposite direction (180 degrees out of phase). This gamma ray is referred to as the annihilation gamma ray. Under the condition that a lot of positron emitter nuclides, such as N-13, are contained in a sample to be measured, the gamma ray measurement of a nuclide to be measured having an energy smaller than the energy (511 keV) of this annihilation gamma ray becomes difficult due to the background radiation caused by Compton scattering of the annihilation gamma ray.

In the present invention, attention is focused on the emission process of a positron of a positron emitter nuclide. The range of a positron depends on its emission energy. Then, the range of a positron, in the case of N-13 (1.19 MeV), is a several-meter range in a gas, and a several-millimeter range in a solid body. That is, most of positrons emitted in a gas combine with negative electrons at a place several-meter away to emit annihilation gamma rays.

On the other hand, an ordinary radiation detector is from 5 cm to about 10 cm or less in diameter, and a measurement cell (a container for containing a measured gas) is provided according to these detector sizes. Accordingly, an ordinary measurement cell is from 5 cm to about 10 cm in diameter. The size of this measurement cell is about double-digit small as compared with the range of a positron, and thus a positron emitted in the measurement cell will immediately reach an inner wall of the measurement cell and emit an annihilation gamma ray in this inner wall.

Figure 3:
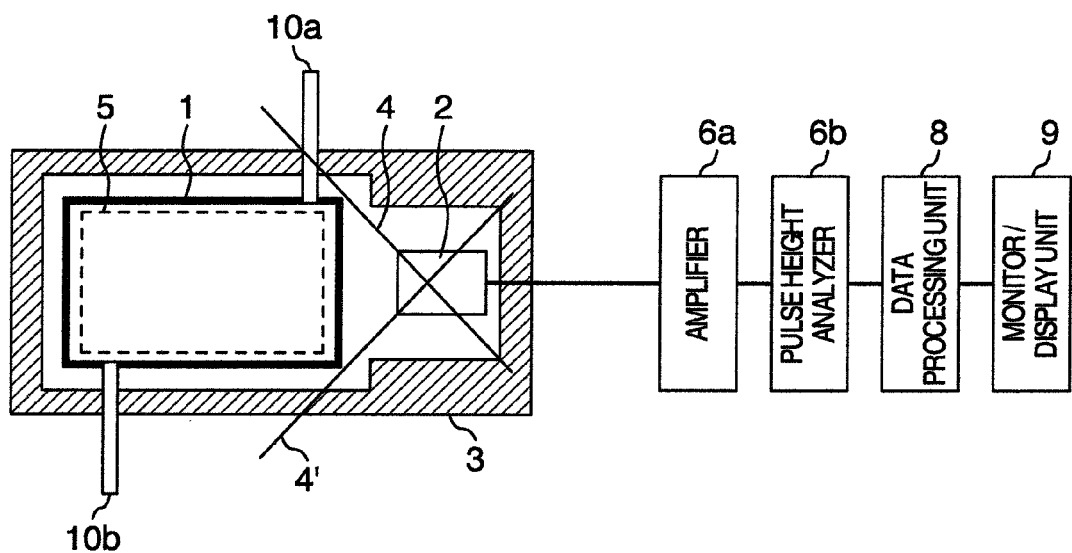
FIG. 3 is a view illustrating the measurement principle of the present invention.

FIG. 3 is a view illustrating the measurement principle of the present invention. A measurement apparatus shown in FIG. 3 is configured suitably for describing the measurement principle of the present invention. That is, in the measurement apparatus shown in FIG. 3, a radiation emitted from the measurement cell 1 provided in the shield 3 is measured with the radiation detector 2, the amplifier 6a, and the pulse height analyzer 6b, and the measured value is analyzed with the data processing unit 8, and this result is displayed in the monitor/display unit 9.

The measured gas sample flows through the inlet/outlet pipes 10a, 10b of the measurement cell 1. The installation relationship between the measurement cell 1 and the radiation detector 2 provided in the shield 3 satisfies a measurement geometry condition for viewing the radiation emitted from the whole measurement cell 1. In the measurement apparatus shown in FIG. 3, the viewing range of radiation measurement is indicated by 4 and 4'.

Figure 17:
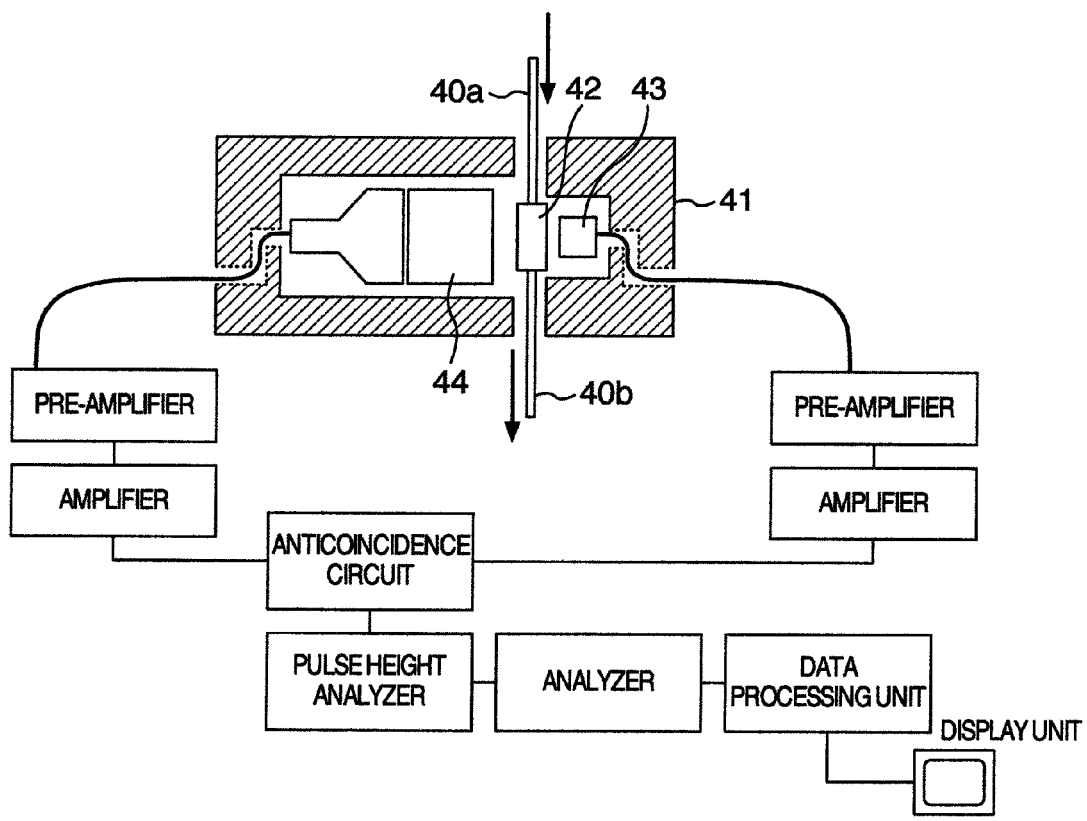
FIG. 17 is a view showing a conventional radioactive gas measurement apparatus.

In the configuration of the measurement apparatus shown in FIG. 3, most of radiations of the measured sample fluid and annihilation gamma rays generated in the inner wall 5 (indicated by a dotted line) of the measurement cell 1 will be measured by the detector 2. For this reason, in the conventional apparatus, unless a special and complicated measuring circuit, such as an anticoincidence circuit as shown in FIG. 17, is employed to perform an annihilation gamma ray suppression processing, an index nuclide (Xe-133 or the like) could not be measured from the measured sample gas with an excellent sensitivity and accuracy.

The present invention has been made based on a new knowledge enabling reduction of the contribution of annihilation gamma rays by taking measures to reduce the inner wall of the measurement cell, which the detector views, as much as possible based on the physical phenomenon of this positron annihilation process. Moreover, this knowledge is implemented by optimally setting the radiation measurement geometry condition which is determined by the collimator provided between the radiation detector and the measurement cell.

Figure 4:
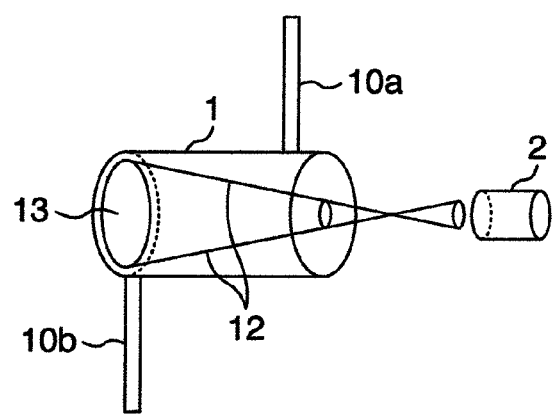
FIG. 4 is a view showing a three-dimensional configuration of a cylindrical measurement cell and a detector of the present invention.

By providing the collimator 11 within the shield 3, an expected measurement range 12 (a range effective for radiation measurement) of radiations emitted from the measurement cell 1 becomes conical. FIG. 1 two-dimensionally shows the relationship between the cylindrical measurement cell 1 and the detector 2. FIG. 4 three-dimensionally shows the arrangement of the cylindrical measurement cell 1 and the detector 2 (illustration of the shield 3 and the collimator 11 is omitted). Under this measurement geometry condition, the amount for the disturbing annihilation gamma rays generated in the inner wall of the measurement cell 1 to enter the detector 2 is limited by a part of the inner wall 13 of the measurement cell 1 facing the detector 2. In the apparatus shown in FIG. 3, an influence of the disturbing annihilation gamma rays can be significantly reduced depending on the ratio for the detector to view the inner wall of the measurement cell 1, as compared with the case where the whole measurement cell 1 is to be measured.

Figure 5:
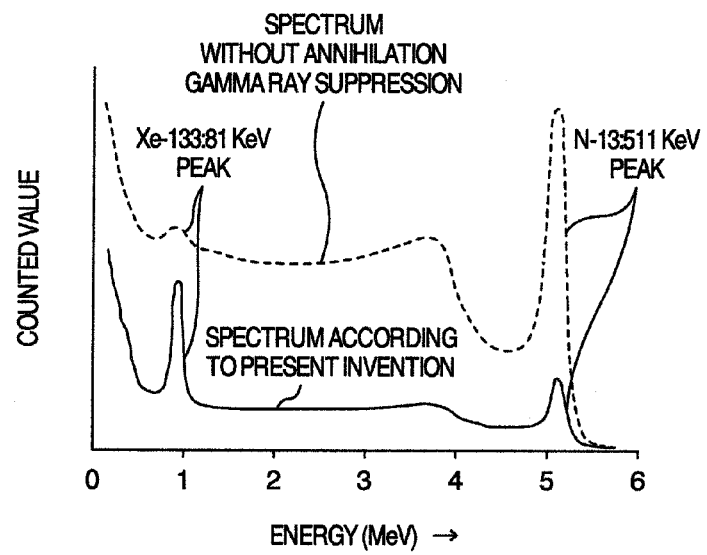
FIG. 5 is a graph showing a spectrum measured by the present invention and a spectrum measured by a conventional example.

FIG. 5 shows a spectrum measured by the present invention and a spectrum measured by a conventional example. It is understood that as compared with the conventional measured spectrum, in the measured spectrum of the present invention, the detected amount of N-13 (511 keV) can be significantly reduced, that the Compton scattering part can be also significantly reduced, and that the nuclide to be measured Xe-133 (81 key), whose energy is smaller than 511 keV, emitted by the annihilation gamma ray can be prominently measured.

Next, the optimum geometry of the collimator 11 and the detector 2 is described. The annihilation gamma ray suppressing effect of the conventional apparatus employing the anticoincidence circuit or the like is 50% to 20%. The measurement geometry condition of the present invention having a suppression effect equivalent to this suppression effect is investigated.

Figures 6A, 6B, 6C:
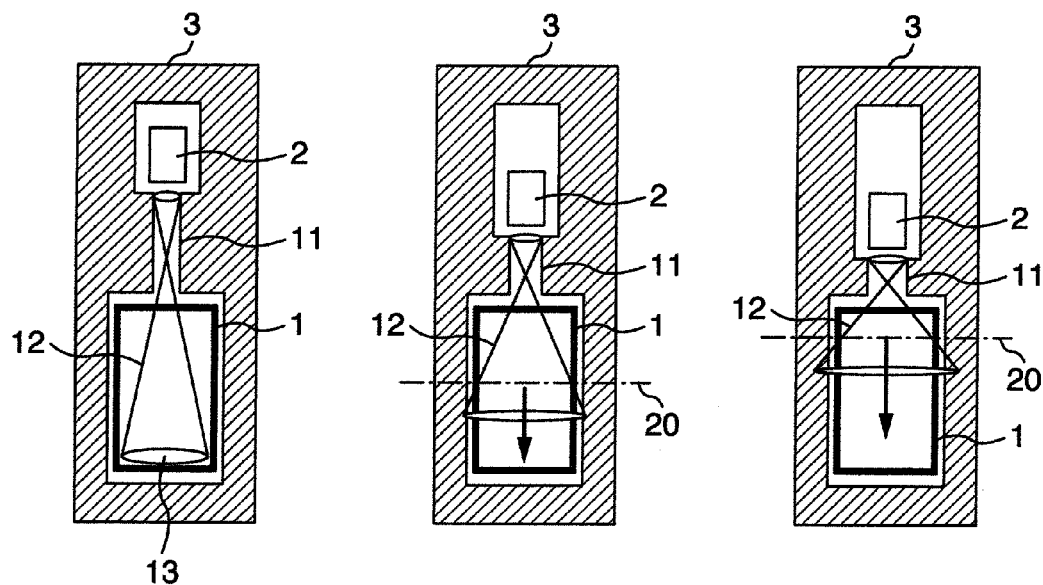
FIG. 6A is a view showing a geometry of a detector and a collimator wherein the measurement cell is viewed under a first condition, in the first embodiment of the present invention.
FIG. 6B is a view showing a geometry of the detector and the collimator wherein the measurement cell is viewed under a second condition, in the first embodiment of the present invention.
FIG. 6C is a view showing a geometry of the detector and the collimator wherein the measurement cell is viewed in under third condition, in the first embodiment of the present invention.

FIGS. 6A-6C each show the geometry of the detector 2 and the collimator 11. In FIGS. 6A-6C, the conditions for the detector 2 to view the cylindrical measurement cell 1 through the collimator 11 differ, respectively. FIG. 6A shows a measurement geometry condition for viewing only the bottom inner wall 13 of the measurement cell 1 facing the detector 2, and the viewing range 12 thereof. The inner wall area of the bottom inner wall 13 of the measurement cell 1 facing the detector 2 indicates the inner wall area of the measurement cell existing at the farthest place in the viewing direction of the radiation detector 2. FIG. 6B shows a measurement geometry condition under which an intercept 20 of the viewing range 12 of the measurement cell 1 is a half the cylindrical body length of the measurement cell 1, and the viewing range 12 thereof. Similarly, FIG. 6C shows a measurement geometry condition under which the intercept 20 of the viewing range 12 is four fifths the cylindrical body length of the measurement cell 1, and the viewing range 12 thereof.

In FIG. 6A, annihilation gamma rays emitted from the bottom inner wall 13 (i.e., the viewing range 12 of the detector 2) of the measurement cell 1 facing the detector 2 and the radiation of the measured sample gas are measured. In FIG. 6B and FIG. 6C, annihilation gamma rays emitted from an inner wall area below the conical intercept 20 in the viewing range 12 of the detector 2 (indicated by arrows in FIG. 6B and FIG. 6C), and the radiation of the measured sample gas are measured. As apparent from FIGS. 6A-6C, the reduction ratio of the annihilation gamma rays of FIG. 6B is about ½ (50%) and the reduction ratio of the annihilation gamma rays of FIG. 6C is about ⅘ (80%). The reduction effect of FIG. 6A is larger than that of FIG. 6B. The relationship of these reduction ratios of the annihilation gamma rays is determined by a ratio of the whole inner wall area (ST) of the measurement cell 1 and an inner wall area (S) which the radiation detector 2 views.

FIGS. 7A-7C each show a measurement geometry condition and the viewing range 12 thereof (the detector and the collimator are not shown). For a cylindrical measurement cell shown in FIG. 7A, a relationship among the measurement geometry conditions shown in FIGS. 6A-6C, the viewing ranges thereof 12, and the reduction ratio of the annihilation gamma rays is satisfied. Moreover, for a vertical column cell of any shape, such as a rectangular measurement cell shown in FIG. 7B, and a hexagon measurement cell shown in FIG. 7C, the same relationship is satisfied. Furthermore, the present invention can be sufficiently applicable also to an irregular-shaped cell, a spherical or elliptic cell, and the like.

FIG. 8 shows a relationship among the whole inner wall area (ST) of the measurement cell 1, the inner wall area (S) which the radiation detector 2 views, and the ratio thereof (the detector and the collimator are not shown). For the diameter D of the vertical cylindrical measurement cell, if the intercept height of the viewing range 12 of the measurement cell 1 determined by an arrangement of the detector and the collimator is h1, the whole inner wall area which the detector views is S (indicated by shading in FIG. 8). Here, the ratio (S/ST) of S and ST is the suppression ratio of annihilation gamma rays. These relationships are described below.

Figure 10:
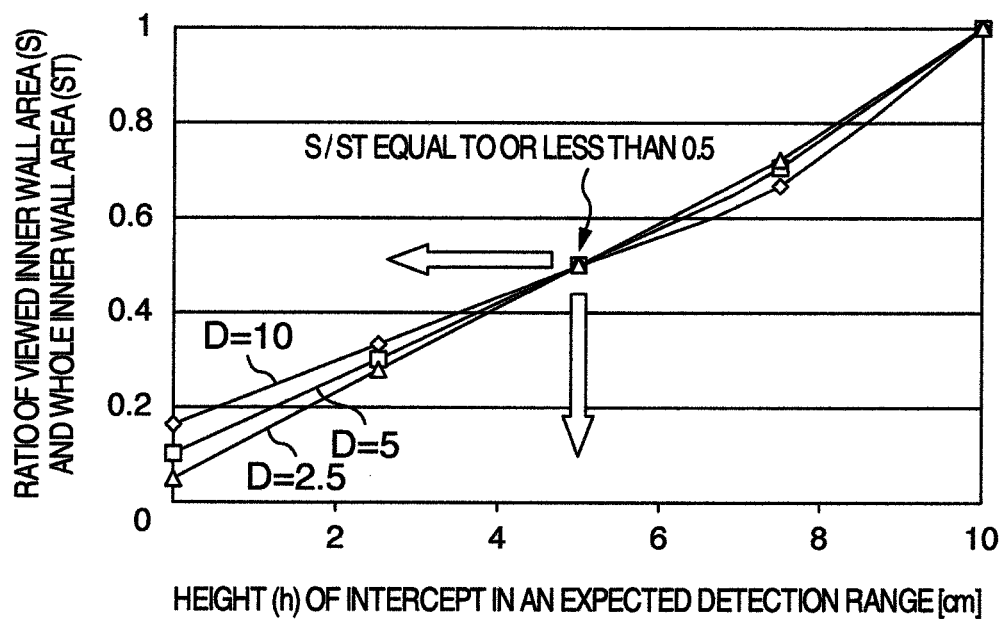
FIG. 10 is a view showing the ratio of an inner wall area viewed by a cylindrical measurement cell and the whole inner wall area.

FIG. 9 is a view showing an example of calculation parameters wherein the diameter D of the measurement cell 1 is 10 cm, and the intercept (h) of the viewing range 12 of the measurement cell 1 is 2.5, 5, 7.5, and 1 cm, respectively. In addition, FIG. 10 is a graph showing the height (h) of the intercept of an expected detection range and the ratio (S/ST) of the inner wall area viewed by the measurement cell and the whole inner wall area when the length (height h) of the vertical cylindrical measurement cell 1 is set to 10 cm. Furthermore, FIG. 10 also shows the results when the parameter of the diameter D of the measurement cell is varied from 10 cm, 5 cm, to 2.5 cm. Note that, through the process of obtaining the results, the area (W portion of FIG. 9) of a window of the measurement cell which the detector views is neglected because the area thereof is small.

As apparent from FIG. 10, when the height of the vertical column measurement cell h=10 cm and the detector views the whole length (10 cm) of the vertical column measurement cell, the S/ST ratio is 1. The condition that the S/ST ratio is 1 indicates a state (capability) where there is no suppression effect of the annihilation gamma ray. Similarly, when the length of the vertical columnar measurement cell which the detector views is a half (the height h=5 cm), the S/ST ratio is 0.5. This indicates that the suppression ratio of the annihilation gamma rays is 50%. Moreover, as the height h of the vertical column measurement cell is reduced further, S/ST will also decrease and S/ST becomes about 0.3 when h=2.5 cm. Furthermore, when the height of the vertical column measurement cell h=0 (when the detector views no side inner wall in the length direction of the measurement cell), S/ST is below 0.2.

In the foregoing, the case where the length of the vertical column measurement cell is 10 cm has been described, however, the same is true even if the diameter D of the measurement cell is varied. That is, even if the length of the vertical column measurement cell is varied, the suppression ratio equal to or less than 50%, which is equivalent to the annihilation gamma ray suppressing effect of the conventional apparatus, can be achieved by designing the intercept of the measurement cell in a range, which the detector views, to equal to or less than a half the cell length.

As described above, according to this embodiment, in the radiation measurement geometry condition determined by the collimator and the radiation detector viewing the measurement cell, the range in which the detector views the measurement cell is set to equal to or less than a half the measurement cell length and thereby a complicated measurement system employing the anticoincidence circuit of the conventional apparatus is eliminated. Moreover, the shield for shielding the whole detection system can be also reduced in volume by a half. Thus, a simple, small, low cost (about ⅓), and practical annihilation gamma ray suppression type measurement apparatus can be realized. Furthermore, a high-performance failed-fuel detection system, which measures and monitors a failed-fuel detection index nuclide in a radioactive gas mixed with positron emitter nuclides as well as detects a failed fuel with high sensitivity and high accuracy can be realized.

A positron annihilation gamma ray suppression type radioactive gas measurement apparatus of a second embodiment of the present invention is described. As the first embodiment of the present invention, the embodiment related to the condition that the detector views the side inner wall of the vertical column measurement cell has been shown, while as the second embodiment of the present invention, an embodiment related to an optimum measurement geometry condition that the detector does not view the side inner wall of the vertical column measurement cell is shown.

Figure 11:
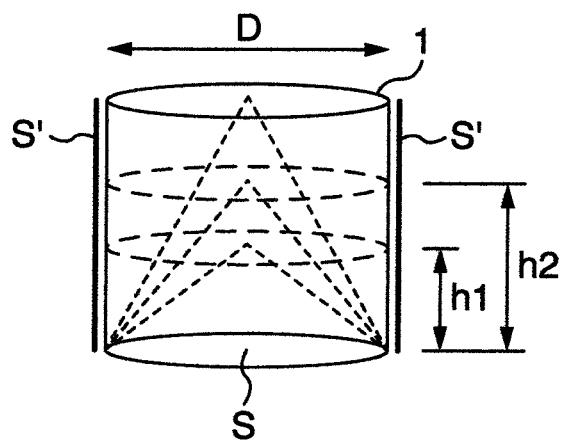
FIG. 11 is a view showing a relationship between the whole inner wall area and the inner wall area viewed by the radiation detector when the detector does not view a side inner wall of the vertical column measurement cell 1.

FIG. 11 is a view showing the case where the detector does not view a side inner wall (S') of the vertical column measurement cell 1, and a relationship between the whole inner wall area (ST) of the measurement cell 1 and the inner wall area (S) which the radiation detector 2 views. The inner wall area (S) herein refers to the inner wall area of a measurement cell existing at the farthest place in the viewing direction of the radiation detector 2, as described above. Note that, in FIG. 11, the illustration of the detector and the collimator is omitted.

If the length (height h1, h2) of the vertical column measurement cell 1 with the diameter D is varied, the ratio (S/ST) of the expected inner wall area (S) of the measurement cell (in this case, the bottom area S of the vertical column measurement cell 1) and the whole inner wall area (ST) also varies greatly. Conceptually, the longer the length of the vertical column measurement cell 1, the smaller the S/ST ratio becomes and the greater the suppression effect of annihilation gamma rays also becomes.

Figure 12:
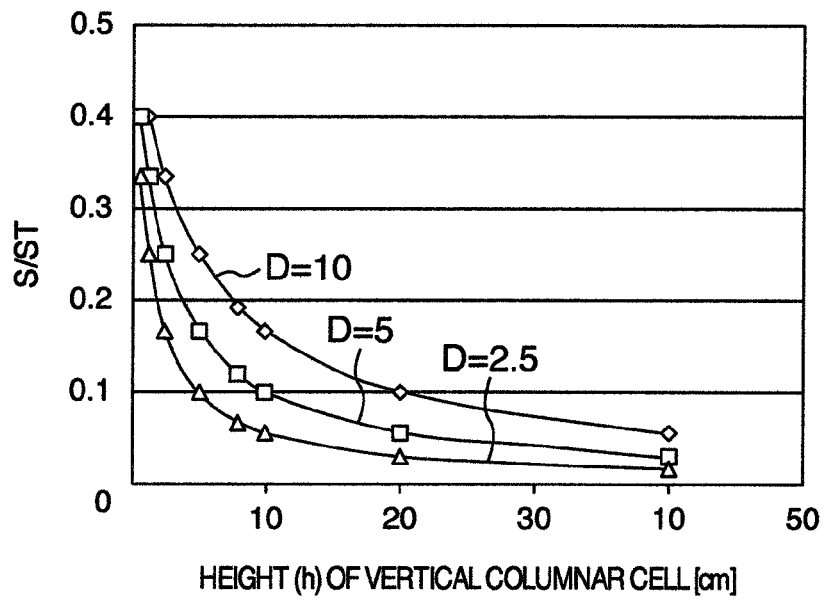
FIG. 12 is a view showing a relationship between the length of the vertical column measurement cell 1 and an S/ST ratio with the diameter D of the vertical column measurement cell 1 as a parameter.

FIG. 12 is a view showing a relationship between the length of the vertical column measurement cell 1 and the S/ST ratio with the diameter D of the vertical column measurement cell 1 as the parameter. As apparent from this result, for each diameter D, as the length (h) of the measurement cell is increased, the S/ST ratio decreases. Moreover, since the suppression effect of annihilation gamma rays of the conventional apparatus is 50% to 20%, it is understood that in order to achieve the effective suppression effect equal to or less than 20% (S/ST equal to or less than 0.2) of the conventional apparatus, the detector's viewing range just needs to be designed so as to secure the cell length (h) equal to or greater then 10 cm in each cell diameter D.

Figure 13:
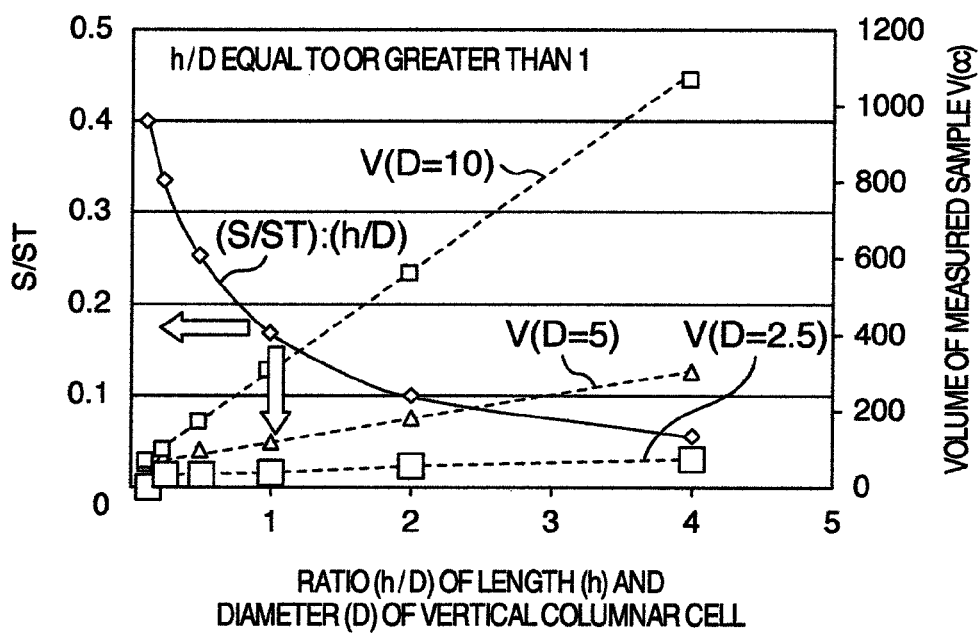
FIG. 13 is a view showing the S/St ratio with the ratio (h/D) of the length (h) and the diameter D of the vertical column measurement cell 1 taken as the horizontal axis.

FIG. 13 is a view showing the calculation result of FIG. 12 with the ratio (h/D) of the length (h) and the diameter D of the vertical column measurement cell 1 taken as the horizontal axis. As apparent from this result, it is understood that if the h/D ratio is designed to be equal to or greater than 1 (indicated by a solid outline arrow on a white background in FIG. 13), it is possible to obtain the S/ST value equal to or less than 0.2 (the suppression effect of annihilation gamma rays is equal to or less than 20%). Moreover, in the view, the relationship among the volume (V) of the measured sample gas viewed by the detector, the diameter D of each measurement cell, and the h/D thereof is shown with the respective dotted lines. The volume (V) of the measured sample gas is directly related to the measurement sensitivity of the index nuclide to be measured. That is, it is important to select any measurement geometry condition under which S/ST becomes equal to or less than 0.2, taking into consideration the volume (V) of the measured sample gas which is viewed by the detector.

Figure 14:
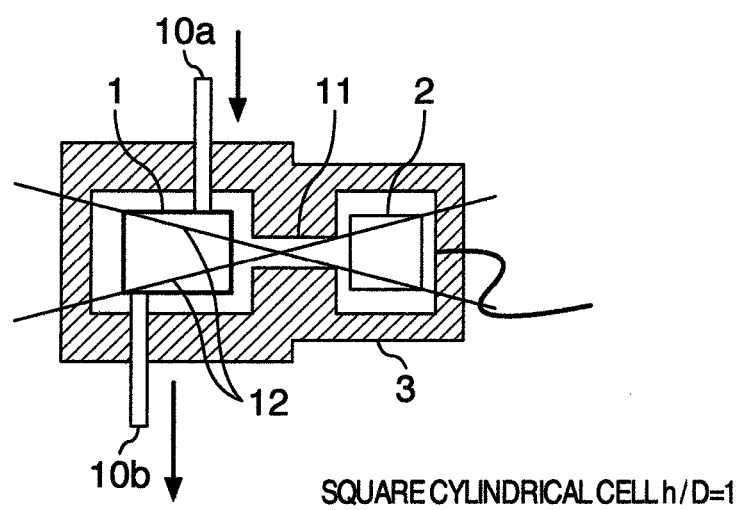
FIG. 14 shows an example of the configuration of the measurement cell, the collimator, and the radiation detector wherein the ratio (h/D) of the length (h) and the diameter D of the vertical columnar measurement cell 1 is 1.

FIG. 14 shows an example of the planar configuration of the measurement cell 1, the collimator 11, and the radiation detector 2 wherein h/D is 1. In FIG. 14, the measured sample gas and the range 12 of the inner wall area viewed by the measurement cell 1 are indicated with a solid line. The configuration shown in FIG. 14 is an example wherein the diameter D of the square cylindrical measurement cell 1 is 5 cm and the length thereof is 5 cm, and wherein S/ST is equal to or less than 0.2 under a design condition of h/D=1. This indicates that the suppression ratio of annihilation gamma rays can be set equal to or less than 20%.

Figure 15:
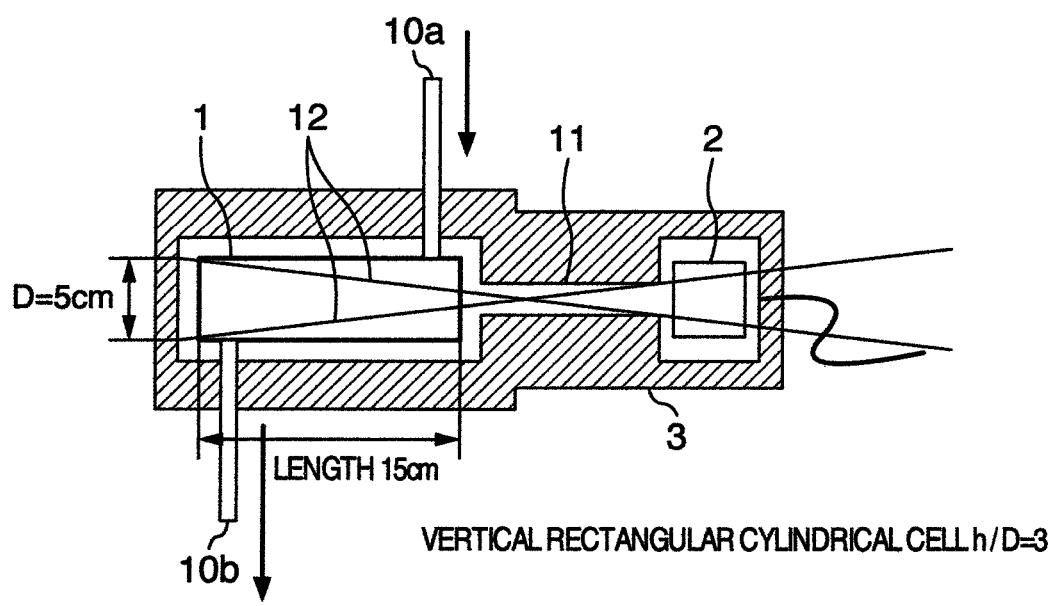
FIG. 15 shows an example of the configuration of the measurement cell, the collimator, and the radiation detector wherein the ratio (h/D) of the length (h) and the diameter D of the vertical columnar measurement cell 1 is 3.

FIG. 15 shows an example of the planar configuration of the measurement cell 1, the collimator 11, and the radiation detector 2 wherein h/D is equal to or greater than 1. In FIG. 15, the measured sample gas and the range 12 of the inner wall area viewed by the measurement cell 1 are indicated with a solid line. The configuration shown in FIG. 15 is an example wherein the diameter D of the vertical rectangular cylindrical measurement cell 1 is 5 cm and the length thereof is 15 cm, and wherein S/ST is equal to or less than 0.08 under a design condition of h/D=3. This indicates that the suppression ratio of annihilation gamma rays can be set equal to or less than 8%, and a significant suppression effect can be achieved as compared with the performance of the conventional apparatus.

In the case where the side inner wall of the vertical columnar measurement cell is not viewed as with this embodiment described above, under the radiation measurement geometry condition determined by the collimator and the radiation detector viewing the measurement cell, the ratio (h/D) of the diameter D (circle diameter) of the vertical columnar measurement cell and the length h is set equal to or greater than 1 and thereby the complicated measurement system employing the anticoincidence circuit of the conventional apparatus is eliminated, and the shield for shielding the whole detection system can be also reduced in volume by a half, and a simple and one-third low cost annihilation gamma ray suppression type measurement apparatus can be realized.

In the foregoing, the vertical columnar measurement cell has been described, however, a measurement cell with any contour can be optimally designed from the length h of the measurement cell viewed by the detector and the diameter D of the inner area of a measurement cell existing at the farthest place in the viewing direction of the detector. Moreover, in the foregoing, the diameter D of the inner area has been described with the collimation shape of the collimator as a circle, however, also for shapes, such as ellipse, square, and hexagon, the optimal design equivalent to that of the circular shape is possible using the diameter D in terms of a circle (circular equivalent diameter) determined by the viewed inner area, and the measurement apparatus similar to the above-described one can be realized. Note that, in this application, the term "circular equivalent diameter" is used in a broad sense including the "circle diameter".

Figure 16:
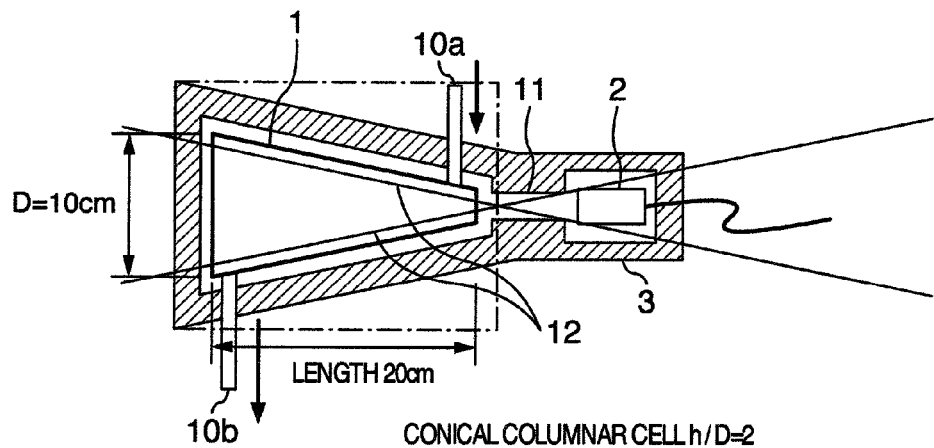
FIG. 16 is a view showing one example of the configuration of the measurement cell, the collimator, and the detector according to a third embodiment of the present invention.

FIG. 16 is a view showing a positron annihilation gamma ray suppression type radioactive gas measurement apparatus of a third embodiment of the present invention. In the radioactive gas measurement apparatus of the third embodiment shown in FIG. 16, a circular cone, triangular pyramid, or square cone measurement cell is used in place of the square vertical columnar measurement cell which is used in the radioactive gas measurement apparatuses of the first embodiment and the second embodiment of the present invention.

The respective design geometry of the detector 2, the collimator 11, and the measurement cell 1, which the radioactive gas measurement apparatus of the third embodiment includes, are the same as those of the detector 2, the collimator 11, and the measurement cell 1 which the radioactive gas measurement apparatuses of the first embodiment and the second embodiment includes. In the third embodiment shown in FIG. 16, a measurement cell having a conical shape along a solid line indicative of the measured sample gas and a range of the inner wall area 12 viewed by the measurement cell 1 is used. The third embodiment shown in FIG. 16 shows an example wherein the diameter D of the bottom area of the conical measurement cell 1 is 10 cm and the length thereof is 20 cm, and wherein S/ST is 0.1 under a design condition of h/D=2. This indicates that the suppression ratio of annihilation gamma rays can be set equal to or less than 10%, and this can exhibit the suppression effect of annihilation gamma rays similar to those of the first embodiment and second embodiment.

In the third embodiment, with regard to the vertical columnar measurement cell, as compared with the shield material required in the first embodiment and second embodiment, the shield material corresponding to a region indicated by a dashed dotted line of FIG. 16 can be reduced significantly. As described above, with the positron annihilation gamma ray suppression type radioactive gas measurement apparatus of the third embodiment, the size of the shield of the detection system can be reduced further, and a reduction in size and cot of the whole apparatus can be achieved.

Other objects, features and advantages of the invention will become apparent from the following description of the embodiments of the invention taken in conjunction with the accompanying drawings.

The invention claimed is:

1. A radioactive gas measurement apparatus comprising:
   a radiation measurement cell comprising an inlet pipe and a discharge pipe, the radiation measurement cell introducing and discharging a radioactive gas containing a nuclide to be measured and a positron emitter nuclide through the inlet pipe and the discharge pipe;
   a radiation detector for measuring a radiation generated from the radioactive gas; and
   a radiation collimator allowing the radiation measurement cell to communicate with the radiation detector and setting a predetermined radiation measurement geometry condition between the radiation measurement cell and the radiation detector, wherein
   as the predetermined radiation measurement geometry condition, an inner wall area of the radiation measurement cell which the radiation detector views through the radiation collimator is set equal to or less than a half of a total inner wall area of the radiation measurement cell.

2. The radioactive gas measurement apparatus according to claim 1, wherein as the predetermined radiation detection geometry condition, under a condition that a side inner wall of the radiation measurement cell is not viewed, a ratio (h/D) of a length (h) of the radiation measurement cell and a circular equivalent diameter (D) of an inner wall area existing at the farthest place of the radiation measurement cell which the radiation detector views is set to equal to or greater than 1.

3. The radioactive gas measurement apparatus according to claim 1, wherein the radiation measurement cell is columnar.

4. The radioactive gas measurement apparatus according to claim 1, wherein the radiation measurement cell is conical.

5. The radioactive gas measurement apparatus according to claim 1, wherein an index nuclide for nuclear reactor failed-fuel detection is measured as the nuclide to be measured, thereby detecting whether or not there is a failed fuel.

6. The radioactive gas measurement apparatus according to claim 2, wherein an index nuclide for nuclear reactor failed-fuel detection is measured as the nuclide to be measured, thereby detecting whether or not there is a failed fuel.

7. The radioactive gas measurement apparatus according to claim 3, wherein an index nuclide for nuclear reactor failed-fuel detection is measured as the nuclide to be measured, thereby detecting whether or not there is a failed fuel.

8. The radioactive gas measurement apparatus according to claim 4, wherein an index nuclide for nuclear reactor failed-fuel detection is measured as the nuclide to be measured, thereby detecting whether or not there is a failed fuel.

9. A failed-fuel detection system comprising:
   a sampler for sampling a radioactive gas containing a nuclide to be measured and a positron emitter nuclide passing through a nuclear reactor fuel housed in a nuclear reactor; and
   a radioactive gas measurement apparatus for measuring a radiation generated from the radioactive gas sampled by the sampler, wherein the radioactive gas measurement apparatus comprises:
   a radiation measurement cell comprising an inlet pipe connected to the sampler and a discharge pipe, the radiation measurement cell introducing and discharging a radioactive gas containing a nuclide to be measured and a positron emitter nuclide through the inlet pipe and the discharge pipe;
   a radiation detector for measuring a radiation generated from the radioactive gas; and
   a radiation collimator allowing the radiation measurement cell to communicate with the radiation detector and setting a predetermined radiation measurement geometry condition between the radiation measurement cell and the radiation detector, and wherein
   as the predetermined radiation measurement geometry condition, an inner wall area of the radiation measurement cell which the radiation detector views through the radiation collimator is set equal to or less than a half of a total inner wall area of the radiation measurement cell.

10. The failed-fuel detection system according to claim 9, wherein as the radiation detection geometry condition, under a condition that a side inner wall of a measurement cell is not viewed, a ratio (h/D) of a length (h) of the radiation measurement cell and a circular equivalent diameter (D) of an inner wall area existing at the farthest place of the radiation measurement cell which the radiation detector views is set to equal to or greater than 1.

* * * * *